United States Patent
Neidlein et al.

(10) Patent No.: US 6,475,957 B1
(45) Date of Patent: Nov. 5, 2002

(54) N-CYCLOALKYL-3-ALKENYBENZOYL-PYRAZOLE DERIVATIVES

(75) Inventors: Ulf Neidlein, Mannheim (DE); Norbert Götz, Worms (DE); Ernst Baumann, Dudenhofen (DE); Wolfgang von Deyn, Neustadt (DE); Steffen Kudis, Mannheim (DE); Roland Götz, Neulussheim (DE); Klaus Langemann, Worms (DE); Guido Mayer, Neustadt (DE); Ulf Misslitz, Neustadt (DE); Matthias Witschel, Ludwigshafen (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/019,047

(22) PCT Filed: Jun. 23, 2000

(86) PCT No.: PCT/EP00/05860

§ 371 (c)(1), (2), (4) Date: Dec. 27, 2001

(87) PCT Pub. No.: WO01/04096

PCT Pub. Date: Jan. 18, 2001

(30) Foreign Application Priority Data

Jul. 9, 1999 (DE) .......................... 199 31 863

(51) Int. Cl.⁷ .......................... A01N 43/56; C07D 231/20
(52) U.S. Cl. ...................... 504/282; 548/369.4
(58) Field of Search .................. 548/366.1, 369.4; 504/282

(56) References Cited

U.S. PATENT DOCUMENTS

| | | |
|---|---|---|
| 5,807,806 A | 9/1998 | Tanaka |
| 6,143,696 A | 11/2000 | Baumann |

FOREIGN PATENT DOCUMENTS

| | | |
|---|---|---|
| EP | 282 944 | 9/1988 |
| EP | 990 649 | 4/2000 |
| WO | 98/42677 | 10/1998 |
| WO | 98/50366 | 11/1998 |
| WO | 98/52926 | 11/1998 |
| WO | 98/56766 | 12/1998 |

OTHER PUBLICATIONS

Derwent 98–557454/47 (1998).

Primary Examiner—Robert W. Ramsuer
(74) Attorney, Agent, or Firm—Keil & Weinkauf

(57) ABSTRACT

Cycloalkyl-substituted benzoylpyrazoles of the formula I

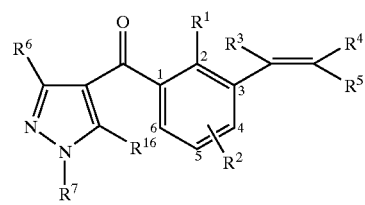

where the variables have, for example, the following meanings:

$R^1$ is hydrogen, nitro, halogen, cyano, thiocyanato, or an unsubstituted or substituted aliphatic radical;

$R^2$ is an unsubstituted or substituted aliphatic radical, halogen, nitro, or substituted sulfonyl or amino groups, $R^3$ is hydrogen, halogen, $C_1$–$C_6$-alkyl, $C_1$–$C_6$-haloalkyl, $C_1$–$C_6$-alkoxy, $C_2$–$C_6$-alkenyl or $C_2$–$C_6$-alkynyl;

$R^4$, $R^5$ are hydrogen, nitro, halogen, cyano, thiocyanato, an unsubstituted or substituted aliphatic radical or substituted sulfonyl or amino groups;

$R^6$ is hydrogen, halogen, $C_1$–$C_6$-alkyl, $C_1$–$C_6$-alkoxy, $C_3$–$C_8$-cycloalkyl;

$R^7$ is a cyclic ring system having 3–14 ring atoms;

$R^{16}$ is hydroxyl or a substituted hydroxyl group;

and their tautomers or agriculturally useful salts are described.

Moreover, the invention describes processes for preparing compounds of the formula I, compositions comprising them, and the use of the compounds of the formula I and of the compositions comprising them for controlling harmful plants.

13 Claims, No Drawings

N-CYCLOALKYL-3-ALKENYBENZOYL-PYRAZOLE DERIVATIVES

This application is a 371 of PCT/EP/00/05860, filed Jun. 23, 2000.

The present invention relates to cycloalkyl-substituted benzoylpyrazoles of the formula I

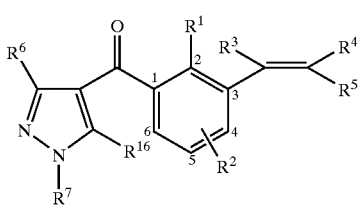

where:
- $R^1$ is hydrogen, nitro, halogen, cyano, thiocyanato, $C_1$–$C_6$-alkyl, $C_1$–$C_6$-haloalkyl, $C_1$–$C_6$-alkoxy, $C_1$–$C_6$-alkylthio, $C_1$–$C_6$-alkoxy-$C_1$–$C_6$-alkyl, $C_2$–$C_6$-alkenyl, $C_2$–$C_6$-alkynyl, $-S(O)_n R^8$, $-SO_2 OR^9$, $-SO_2NR^9R^{10}$, $-NR^{10}SO_2R^{11}$, $-NR^{10}COR^{11}$, $-PO(OR^{12})(OR^{13})$;
- $R^2$ is hydrogen, $C_1$–$C_6$-alkyl, $C_1$–$C_6$-alkoxy, $C_1$–$C_6$-alkylthio, $C_2$–$C_6$-alkenyl, $C_2$–$C_6$-alkynyl, halogen, nitro, $-S(O)_n R^8$, $-SO_2 OR^9$, $-SO_2NR^9R^{10}$, $-NR^{10}SO_2R^{11}$, $-NR^{10}COR^{11}$, $-PO(OR^{12})(OR^{13})$;
- $R^3$ is hydrogen, halogen, $C_1$–$C_6$-alkyl, $C_1$–$C_6$-haloalkyl, $C_1$–$C_6$-alkoxy, $C_2$–$C_6$-alkenyl or $C_2$–$C_6$-alkynyl;
- $R^4$, $R^5$ are hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, $-COR^{12}$, $-CO_2R^{12}$, $-COSR^{12}$, $-CONR^{12}R^{13}$, $-C(R^{14})=NR^{15}$, $-PO(OR^{12})(OR^{13})$, $C_1$–$C_4$-alkyl carrying a radical from the following group: $-COR^{12}$, $-CO_2R^{12}$, $-COSR^{12}$, $-CONR^{12}R^{13}$ or $-C(R^{14})=NR^{15}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, where the six last-mentioned radicals may be substituted;
- $R^4$ and $R^5$ together form a $C_2$–$C_6$-alkanediyl chain which can be mono- to tetrasubstituted by $C_1$–$C_4$-alkyl and/or may be interrupted by oxygen or sulfur or an unsubstituted or $C_1$–$C_4$-alkyl-substituted nitrogen;
- $R^6$ is hydrogen, halogen, $C_1$–$C_6$-alkyl, $C_1$–$C_6$-alkoxy, $C_3$–$C_8$-cycloalkyl;
- $R^7$ is a cyclic ring system having 3–14 ring atoms which is unsubstituted or substituted by $C_1$–$C_6$-alkyl, $C_1$–$C_6$-alkoxy, $C_1$–$C_6$-haloalkyl, $C_1$–$C_6$-haloalkoxy, halogen; or is $C_1$–$C_6$-alkyl which is substituted by a cyclic ring system;
- n is 0, 1 or 2;
- $R^8$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
- $R^9$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
- $R^{10}$ is hydrogen or $C_1$–$C_6$-alkyl;
- $R^{11}$ is $C_1$–$C_6$-alkyl or $C_1$–$C_6$-haloalkyl;
- $R^{12}$ is hydrogen, $C_1$–$C_6$-alkyl, $C_3$–$C_6$-cycloalkyl, $C_1$–$C_6$-haloalkyl, $C_3$–$C_6$-alkenyl, $C_3$–$C_6$-alkynyl, phenyl or benzyl, where the two last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;
- $R^{13}$ is hydrogen, $C_1$–$C_6$-alkyl, $C_3$–$C_6$-alkenyl or $C_3$–$C_6$-alkynyl; or
- $R^{12}$ and $R^{13}$ together form a $C_2$–$C_6$-alkanediyl chain which may be mono- to tetrasubstituted by $C_1$–$C_4$-alkyl and/or may be interrupted by oxygen or sulfur or an unsubstituted or $C_1$–$C_4$-alkyl-substituted nitrogen;
- $R^{14}$ is hydrogen, $C_1$–$C_6$-alkyl, $C_1$–$C_6$-haloalkyl, $C_1$–$C_6$-alkoxy, $C_1$–$C_6$-alkoxycarbonyl, $C_3$–$C_6$-cycloalkyl, $C_2$–$C_6$-alkenyl, $C_2$–$C_6$-alkynyl, phenyl or benzyl, where the two last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;
- $R^{15}$ is $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkoxy, $C_1$–$C_6$-haloalkoxy, $C_3$–$C_6$-cycloalkoxy, $C_3$–$C_6$-alkenyloxy, $C_3$–$C_6$-alkynyloxy, phenyl, benzyl or benzyloxy, where the three last-mentioned radicals may be partially or fully halogenated and/or may carry one to three radicals from the following group:
  nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;
- $R^{16}$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, phenyl-$C_1$–$C_4$-alkoxy, phenylcarbonyloxy, phenylcarbonyl-$C_1$–$C_4$-alkoxy, phenylsulfonyloxy, where the phenyl radical of the four last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

and their tautomers or agriculturally useful salts.

Moreover, the invention relates to processes for preparing compounds of the formula I, to compositions comprising them, and to the use of the compounds of the formula I and of the compositions comprising them for controlling harmful plants.

Herbicidally active compounds of the class of the benzoylpyrazoles are disclosed in EP-A 282 944; WO 98/42677; WO 45 98/45273; WO 98/50366; WO 98/52926; WO 98/56766; US 5,807,806.

However, the herbicidal properties of these compounds and their compatability with crop plants are not entirely satisfactory. It is an object of the present invention to provide novel compounds having improved properties which can be used as active compounds in crop protection, in particular as herbicides.

We have found that this object is achieved by the benzoylpyrazoles defined above, which are substituted in the 1 position of the pyrazole derivative by a cyclic ring system.

Furthermore, we have found highly active herbicidal compositions which comprise the compounds I. Moreover, we have found processes for preparing these compositions and methods for controlling or reducing undesirable vegetation using the compounds I.

The present invention also provides stereoisomers of the compounds of the formula I. This includes both pure stereoisomers and mixtures thereof.

The compounds of the formula I contain a carbon-carbon double bond and are therefore present as E isomers or as Z isomers or as E/Z isomer mixtures. Furthermore, the compounds of the formula I can contain further carbon or carbon-nitrogen double bonds. The invention provides both the pure geometric isomers and mixtures thereof.

Likewise, depending on the substitution pattern, the compounds of the formula I can contain one or more chiral centers, in which case they are present as enantiomers or diastereomer mixtures. The invention provides both the pure enantiomers or diastereomers and mixtures thereof.

The compounds of the formula I can also be present in the form of their tautomers or as tautomer mixtures. The tautomeric forms result in particular owing to the hydroxyl substituent at the pyrazole ring. Thus, the compounds can be referred to both as 5-hydroxypyrazoles and as 5-oxopyrazolines.

The compounds of the formula I can also be present in the form of their agriculturally useful salts, the type of salt generally being immaterial. In general, the salts of those cations or the acid addition salts of those acids are suitable whose cations and anions, respectively, do not adversely affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl or hydroxy-$C_1$–$C_4$-alkyl and/or one phenyl or benzyl, preferably diisopropylammonium, tetramethylammonium, tetrabutylammonium, trimethylbenzylammonium, furthermore phosphonium ions, sulfonium ions, preferably tri ($C_1$–$C_4$-alkyl)sulfonium and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, bicarbonate, carbonate, hexafluorosilicate, hexafluorophosphate, benzoate and the anions of $C_1$–$C_4$-alkanoic acids, preferably formate, acetate, propionate and butyrate.

The organic molecular moieties mentioned for the substituents $R^1$–$R^{16}$ are collective terms for individual enumerations of the individual group members. All hydrocarbon chains, i.e. all alkyl, haloalkyl, cycloalkyl, alkoxyalkyl, alkoxy, haloalkoxy, cycloalkoxy, alkylthio, alkylsulfonyl, haloalkylsulfonyl, alkylcarbonyl, haloalkylcarbonyl, alkoxycarbonyl, alkenyl, cycloalkenyl, alkynyl, alkenyloxy, and alkynyloxy moieties can be straight-chain or branched. Unless indicated otherwise, halogenated substituents preferably carry one to five identical or different halogen atoms. The term halogen in each case denotes fluorine, chlorine, bromine or iodine.

Examples of other meanings are:

$C_2$–$C_4$-alkyl: ethyl, n-propyl, 1-methylethyl, butyl, 1-methylpropyl, 2-methylpropyl or 1,1-dimethylethyl;

$C_1$–$C_4$-alkyl, and the alkyl moieties of, for example, $C_1$–$C_4$-alkylcarbonyl heterocyclyl-$C_1$–$C_4$-alkyl, phenyl-$C_1$–$C_4$-alkyl and hetaryl-$C_1$–$C_4$-alkyl: $C_2$–$C_4$-alkyl as mentioned above, and also methyl;

$C_2$–$C_6$-alkyl, and the alkyl moieties of, for example, $C_1$–$C_6$-alkoxy-$C_2$–$C_6$-alkyl: $C_2$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_6$-alkyl, and the alkyl moieties of, for example, $C_1$–$C_6$-alkoxy-$C_1$–$C_6$-alkyl and $C_1$–$C_6$-alkylcarbonyl: $C_2$–$C_6$-alkyl as mentioned above, and also methyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl,1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of $C_1$–$C_6$-haloalkylcarbonyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy, and the alkoxy moieties of $C_1$–$C_4$-alkoxycarbonyl: methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of $C_1$–$C_6$-alkoxy-$C_1$–$C_6$-alkyl, $C_1$–C6-alkoxy-$C_2$–$C_6$-alkyl and $C_1$–$C_6$-alkoxycarbonyl: $C_1$–$C_4$-alkoxy as mentioned above, and also pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy, as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_6$-alkylthio: for example, methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_6$-alkylsulfonyl ($C_1$–$C_6$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, i.e. fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3- dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl;

$C_2$–$C_6$-alkynyl: $C_3$–$C_6$-alkynyl, as mentioned above, and also ethynyl;

$C_3$–$C_6$-alkynyloxy: for example prop-1-yn-1-yloxy, prop-2-yn-1-yloxy, but-1-yn-1-yloxy, but-1-yn-3-yloxy, but-1-yn-4-yloxy, but-2-yn-1-yloxy, pent-1-yn-1-yloxy, pent-1-yn-3-yloxy, pent-1-yn-4-yloxy, pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, hex-1-yn-1-yloxy, hex-1-yn-3-yloxy, hex-1-yn-4-yloxy, hex-1-yn-5-yloxy, hex-1-yn-6-yloxy, hex-2-yn-1-yloxy, hex-2-yn-4-yloxy, hex-2-yn-5-yloxy, hex-2-yn-6-yloxy, hex-3-yn-1-yloxy, hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy;

$C_3$–$C_6$-cycloalkyl: cyclopropyl, cyclobutyl, cyclopentyl or cyclohexyl;

$C_3$–$C_6$-cycloalkoxy: cyclopropoxy, cyclobutoxy, cyclopentoxy or cyclohexoxy;

$C_3$–$C_6$-cycloalkenyl: cyclopropen-1-yl, cyclobuten-1-yl, cyclobuten-3-yl, cyclopenten-1-yl, cyclopenten-3-yl, cyclohexen-1-yl, cyclohexen-3-yl or cyclohexen-4-yl;

heterocyclyl, and the heterocyclyl radicals in heterocyclyloxy and heterocyclyl-$C_1$–$C_4$-alkyl: three- to seven-membered saturated or partially unsaturated mono- or polycyclic heterocycles containing one to three heteroatoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 1,3-dioxolan-4-yl, 1,3-dithiolan-2-yl, 1,3-dithiolan-4-yl, 1,3-dioxan-2-yl, 1,3-dioxan-4-yl, 1,3-dioxan-5-yl, 1,3-dithian-2-yl, 1,3-dithian-4-yl, 1,3-dithian-5-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl or 1,3-dihydrooxazin-2-yl;

hetaryl, and the heteraryl radicals in hetaryloxy and hetaryl-$C_1$–$C_4$-alkyl: aromatic mono- or polycyclic radicals which, in addition to carbon ring members, may additionally contain one to four nitrogen atoms or one to three nitrogen atoms and one oxygen or one sulfur atom or one oxygen or one sulfur atom, for example, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5- triazin-2-yl, 1,2,4-triazin-3-yl, 1,2,4,5-tetrazin-3-yl, and the corresponding benzo-fused derivatives;

$C_2$–$C_6$-alkanediyl: for example ethane-1,2-diyl, propane-1,3-diyl, butane-1,4-diyl, pentane-1,5-diyl or hexane-1,6-diyl;

cyclic ring system having 3–14 ring atoms: $C_3$–$C_8$-cycloalkyl, in particular $C_3$–$C_6$-cycloalkyl as mentioned above, furthermore cycloheptyl or cyclooctyl; $C_3$–$C_8$-cycloalkenyl as mentioned above; bi- or tricyclic carbocyclic or heterocyclic ring systems having up to 14 ring atoms, where the ring systems may be saturated or unsaturated and may contain one, two or three double bonds, and where the heteroatoms in the case of the heterocyclic rings are selected from the group consisting of nitrogen, sulfur and/or oxygen. Carbocyclic bi- or tricyclic ring systems are, for example, adamantyl, norbornyl, camphyl or camphenyl. The bi- or tricyclic ring systems can be unsubstituted or mono- or polysubstituted by $C_1$–$C_6$-alkyl, $C_1$–$C_6$-alkoxy, $C_1$–$C_6$-haloalkyl, $C_1$–$C_6$-haloalkoxy or halogen.

$C_1$–$C_6$-alkyl, which is substituted by a cyclic ring system having 3–14 ring atoms: a straight-chain or branched $C_1$–$C_6$-alkyl group which is substituted by the above-mentioned $C_3$–$C_6$-cycloalkyl groups, $C_3$–$C_6$-cycloalkenyl groups or by carbocyclic or heterocyclic ring systems having up to 14 ring atoms. The following radicals may be mentioned by way of example: cyclopropylmethyl, 1-cyclopropylethyl, 2-cyclopropylethyl, 1-methyl-1-cyclopropylethyl, adamantylmethyl, norbornylmethyl, camphylmethyl or camphenylmethyl. These ring systems can be unsubstituted or mono- or polysubstituted by $C_1$–$C_6$-alkyl, $C_1$–$C_6$-alkoxy, $C_1$–$C_6$-haloalkyl, $C_1$–$C_6$-haloalkoxy or halogen.

All phenyl, hetaryl and heterocyclyl rings are preferably unsubstituted or carry one to three halogen atoms and/or one or two radicals from the following group: nitro, cyano, methyl, trifluoromethyl, methoxy, trifluoromethoxy or methoxycarbonyl.

With respect to the use of the compounds of the formula I according to the invention as herbicides, the variables preferably have the following meanings, in each case on their own or in combination with one another:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$ or —$S(O)_nR^8$; in particular nitro, fluorine, chlorine, bromine, methyl, ethyl, methoxy; preferably chlorine, methyl or methoxy.

$R^2$ is hydrogen, nitro, halogen, cyano, thiocyanato, $C_1$–$C_6$-alkyl., $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$ or —$S(O)_nR^8$; particularly preferably hydrogen, nitro, halogen, such as, for example, fluorine, chlorine or bromine, $C_1$–$C_6$-alkyl, $C_1$–$C_6$-haloalkyl, —$OR^6$ or —$SO_2R^8$; in particular nitro, halogen such as, for example, fluorine, chlorine or bromine, $C_1$–$C_6$-alkyl, $C_1$–$C_6$-haloalkyl, —$OR^6$ or $SO_2R^8$; preferably —$SO_2$—$R^8$, where $R^8$ is $C_1$–$C_6$-alkyl, in particular methyl or ethyl. The substituent $R^2$ is preferably in the 4 or 5 position of the phenyl ring, in particular in the 4 position, i.e. in the position para to the pyrazolecarbonyl group.

$R^3$ is hydrogen, halogen, $C_1$–$C_6$-alkyl, $C_1$–$C_6$-haloalkyl, $C_1$–$C_6$-alkoxy, $C_2$–$C_6$-alkenyl or $C_2$–$C_6$-alkynyl; particularly preferably hydrogen, halogen, such as, for example, fluorine, chlorine or bromine, $C_1$–$C_4$-alkyl, such as, for example, methyl or ethyl, $C_1$–$C_4$-haloalkyl, such as, for example, trifluoromethyl, $C_1$–$C_4$-alkoxy, such as, for example, methoxy or ethoxy, allyl or propargyl; with particular preference hydrogen or methyl;

$R^4$ is hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —$COR^{12}$, —$CO_2R^{12}$, —$COSR^{12}$, —$CONR^{12}R^{13}$, —$C(R^{14})$=$NR^{15}$, —$PO(OR^{12})(OR^{13})$, $C_1$–$C_4$-alkyl, which carries a radical from the following group: —$COR^{12}$, —$CO_2R^{12}$, —$COSR^{12}$, —$CONR^{12}R^{13}$ or —$C(R^{14})$=$NR^{15}$; heterocyclyl,heterocyclyl-$C_1$–$C_4$-alkyl, phenyl, phenyl-$C_1$–$C_4$-alkyl, hetaryl or hetaryl-$C_1$–$C_4$-alkyl, where the six last-mentioned radicals for their part may be substituted by one to three halogen atoms and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl; in particular hydrogen.

$R^5$ is hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —$COR^{12}$, —$CO_2R^{12}$, —$COSR^{12}$, —$CONR^{12}R^{13}$, —$C(R^{14})$=$NR^{15}$, —$PO(OR^{12})(OR^{13})$, $C_1$–$C_4$-alkyl, which carries a radical from the following group: —$COR^{12}$, —$CO_2R^{12}$, —$COSR^{12}$, —$CONR^{12}R^{13}$ or —$C(R^{14})$=$NR^{15}$; heterocyclyl,heterocyclyl-$C_1$–$C_4$-alkyl, phenyl, phenyl-$C_1$–$C_4$-alkyl, hetaryl or hetaryl-$C_1$–$C_4$-alkyl, where the six last-mentioned radicals for their part may be substituted by one to three halogen atoms and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl; particularly preferably hydrogen, halogen, cyano, thiocyanato, $C_1$–$C_6$-alkyl, $C_1$–$C_6$-haloalkyl, —$COR^{12}$, —$CO_2R^{12}$, —$COSR^{12}$, —$CONR^{12}R^{13}$ or —$PO(OR^{12})(OR^{13})$; in particular hydrogen.

$R^6$ is hydrogen, methyl; in particular hydrogen.

$R^7$ is cyclopropyl, cyclopentyl, cyclohexyl, adamantyl, norbornyl, camphyl or camphenyl, which are unsubstituted or mono- or disubstituted by $C_1$–$C_6$-alkyl, in particular methyl.

$R^8$ is $C_1$–$C_6$-alkyl, in particular methyl, ethyl;

$R^9$ is hydrogen, $C_1$–$C_6$-alkyl;

$R^{10}$ is hydrogen, $C_1$–$C_6$-alkyl;

$R^{11}$ is $C_1$–$C_6$-alkyl, $C_1$–$C_6$-alkoxy;

$R^{12}$ is hydrogen, $C_1$–$C_6$-alkyl;

$R^{13}$ is hydrogen, $C_1$–$C_6$-alkyl;

$R^{14}$ is hydrogen, $C_1$–$C_6$-alkyl;

$R^{15}$ is hydrogen, $C_1$–$C_6$-alkyl, $C_1$–$C_6$-alkoxy;

$R^{16}$ is hydroxyl.

In this context, particular preference is given to compounds of the formula I where $R^1$–$R^7$ are each independently of one another as defined below:

$R^1$ is chlorine, methyl, methoxy;

$R^2$ is methylsulfonyl, ethylsulfonyl;

$R^3$ is hydrogen, $R^4$ is hydrogen, $R^5$ is hydrogen, $R^6$ is hydrogen, $R^7$ is cyclopropyl, cyclopentyl, adamantyl, norbornyl, camphyl or camphenyl, which are unsubstituted or mono- or disubstituted by methyl.

Particular preference is given to compounds of the formula I having the radicals $R^1$–$R^{16}$ below or one or more combinations a)–g) of such radicals:

a) $R^1$=$C_1$–$C_6$-alkyl; halogen; $C_1$–$C_6$-alkoxy.

b) $R^2$=$C_1$–$C_6$-alkylsulfonyl; where $R^2$ is preferably located in the position para to the pyrazolylcarbonyl group on the phenyl ring.

c) $R^3$=$R^4$=hydrogen.

d) $R^5$=hydrogen or $C_1$–$C_6$-alkyl.

e) $R^6$=hydrogen.

f) $R^7$=cyclopropyl, cyclopentyl.

g) $R^{16}$=hydroxyl or phenylsulfonyloxy.

Preferred embodiments are the following compounds of the formulae Ia1–Ia6:

TABLE 1

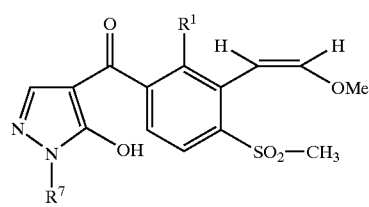

Ia1

| No. | $R^1$ | $R^7$ |
|---|---|---|
| Ia1.001 | O—CH₃ | cyclopropyl |
| Ia1.002 | Cl | cyclopropyl |
| Ia1.003 | CH₃ | cyclopropyl |
| Ia1.004 | O—CH₃ | cyclopentyl |
| Ia1.005 | Cl | cyclopentyl |
| Ia1.006 | CH₃ | cyclopentyl |
| Ia1.007 | O—CH₃ | norbornyl |
| Ia1.008 | Cl | norbornyl |
| Ia1.009 | CH₃ | norbornyl |
| Ia1.010 | O—CH₃ | 2,7,7-trimethylnorbornyl |
| Ia1.011 | Cl | 2,7,7-trimethylnorbornyl |
| Ia1.012 | CH₃ | 2,7,7-trimethylnorbornyl |
| Ia1.013 | O—CH₃ | 2-adamantyl |
| Ia1.014 | Cl | 2-adamantyl |
| Ia1.015 | CH₃ | 2-adamantyl |
| Ia1.016 | O—CH₃ | 7-adamantyl |
| Ia1.017 | Cl | 7-adamantyl |
| Ia1.018 | CH₃ | 7-adamantyl |

Preference is furthermore given to the compounds Ia2, in particular the compounds Ia2.001–Ia2.018, which differ from the corresponding compounds Ia1.001–Ia1.018 in that $R^5$ in the formula I is methoxy:

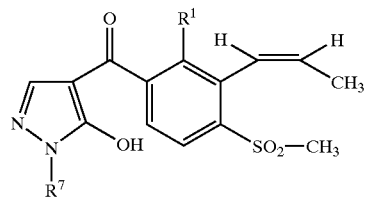

Ia2

Preference is furthermore given to the compounds Ia3, in particular the compounds Ia3.001–Ia3.018, which differ from the corresponding compounds Ia1.001–Ia1.018 in that $R^5$ in the formula I is methyl:

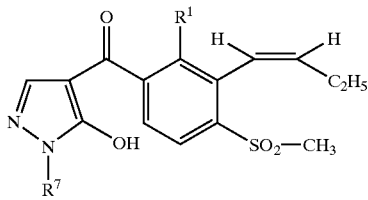

Ia3

Preference is furthermore given to the compounds Ia4, in particular the compounds Ia4.001–Ia4.018, which differ from the corresponding compounds Ia1.001–Ia1.018 in that $R^5$ in the formula I is ethyl:

Ia4

Preference is furthermore given to the compounds Ia5, in particular the compounds Ia5.001–Ia5.018, which differ from the corresponding compounds Ia1.001–Ia1.018 in that $R^5$ in the formula I is cyano:

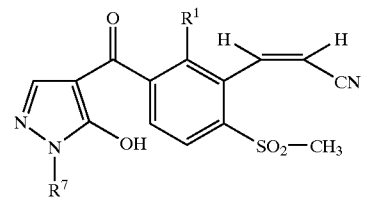

Ia5

Preference is furthermore given to the compounds Ia6, in particular the compounds Ia6.001–Ia6.018, which differ from the corresponding compounds Ia1.001–Ia1.018 in that $R^5$ in the formula I is isopropyl:

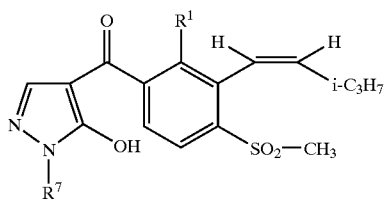

Ia6

The compounds of the formula I are essentially prepared by the processes described in WO 98/50366.

Particularly suitable is a process which comprises acylating a pyrazole of the formula II

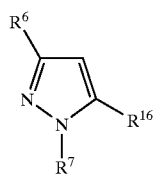

with a carboxylic acid III or an activated derivative thereof

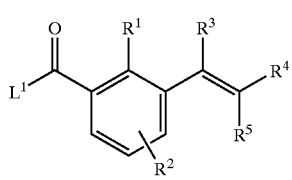

where the variables $R^1$ to $R^5$ are as defined under claim 1 and $L^1$ is hydroxyl or a nucleophilically displaceable leaving group (e.g. halogen, anhydride), and rearranging the acylation product, if appropriate in the presence of a catalyst, to give the compounds I.

Compounds of the formula II are known from the literature or are commercially available. Alternatively, compounds of the formula II can be prepared by the process described in DE 19910505.

Compounds of the formula III are disclosed, inter alia, in WO 98/50366 and the literature references cited therein.

In the reaction scheme below, a synthesis route for preparing compounds I starting from compounds A via the intermediates B, C and D is described in an exemplary manner for $R^1$=methoxy, $R^2$=methylsulfonyl, $R^3$=$R^4$=$R^5$=$R^6$=H, $R^7$=cyclopropyl (Kt—Bu=potassium tert-butoxide; n-Buli=n-butyllithium; ACOH=acetic acid; DME=dimethylethoxyethane).

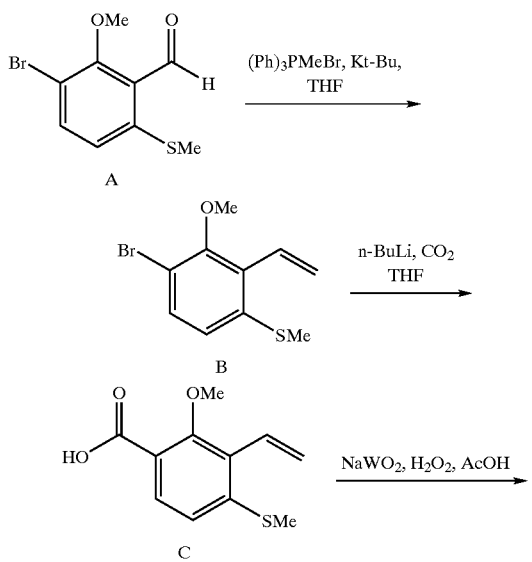

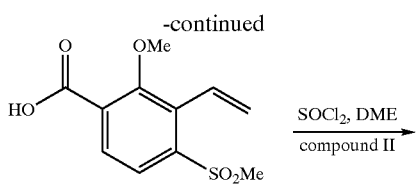

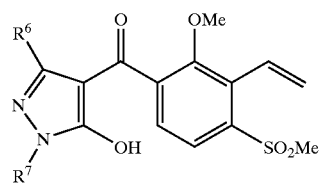

The compounds I can be present in the form of their agriculturally useful salts, the type of salt generally not being important. Suitable salts are usually the salts of those bases which do not adversely affect the herbicidal action of I.

Suitable basic salts are, in particular, those of the alkali metals, preferably the lithium, sodium and potassium salts, those of the alkaline earth metals, preferably calcium, magnesium and barium salts, and those of the transition metals, preferably manganese, copper, zinc and iron salts, ammonium salts, and ammonium salts which may carry one to four $C_1$–$C_4$-alkyl, or hydroxy-$C_1$–$C_4$-alkyl substituents, one phenyl or benzyl substituent, preferably diethylammonium, diisopropylammonium, tetramethylammonium, tetrabutylammonium, trimethylbenzylammonium, and trimethyl(2-hydroxyethyl)ammonium salts, the phosphonium salts, the sulfonium salts, preferably tri($C_1$–$C_4$-alkyl) sulfonium salts, and the sulfoxonium salts, preferably tri ($C_1$–$C_4$-alkyl)sulfoxonium salts.

The compounds I and their agriculturally useful salts are suitable, both in the form of isomer mixtures and in the form of the pure isomers, as herbicides. They can also be used as growth regulators for plants (harmful plants, crop plants and useful plants). The herbicidal compositions comprising the compounds I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds I, or the compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medi-

*cago sativa, Musa* spec., *Nicotiana tabacum (N.rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (s. *vulgare), Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The herbicidal compositions or the active compounds can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The compounds I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended aims; in any case, they should ensure a very fine distribution of the active compounds according to the invention.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the compounds I, either as such or dissolved in an oil or solvent, can be homogenized in water by means of a wetting agent, tackifier, dispersant or emulsifier. Alternatively, it is possible to prepare concentrates comprising active substance, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise from 0.001 to 98% by weight, preferably 0.01 to 95% by weight, of at least one active compound. The active compounds are employed in a purity of from 90% to 100%, preferably 95% to 100% (according to the NMR spectrum).

The compounds I according to the invention can be formulated, for example, as follows:

I 20 parts by weight of a compound I are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of the calcium salt of dodecylbenzenesulfonic acid and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II 20 parts by weight of a compound I are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III 20 parts by weight of a compound I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV 20 parts by weight of an active compound of the formula I are mixed thoroughly with 3 parts by weight of the sodium salt of diisobutylnaphthalenesulfonic acid, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V 3 parts by weight of an active compound of the formula I are mixed with 97 parts by weight of finely divided kaolin. This gives a dust which comprises 3% by weight of the active compound.

VI 20 parts by weight of a compound I are mixed intimately with 2 parts by weight of the calcium salt of dodecylbenzenesulfonic acid, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of a compound I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of a compound I is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the activity spectrum and to achieve synergistic effects, the compounds I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het) aryloxyalkanoic acid and its derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The application rates of active compound are from 0.001 to 3.0, preferably 0.01 to 1.0, kg/ha of active substance (a.s.), depending on the control target, the season, the target plants and the growth stage.

EXAMPLE 1

(5-Methoxy-1-cyclopropyl-1H-pyrazol-4-yl)(4-methylsulfonyl-2-methoxy-3-vinylphenyl) methanone a) 2-Methoxy-6-methylsulfanylbenzaldehyde At 0° C., NaSMe (12.2 g, 0.18 mol) was added a little at a time to a solution of 2-chloro-6-methoxybenzaldehyde (20 g, 0.12 mol) in NMP (12.2 g, 0.18 mol). The solution was stirred at 0° C. for 3 h, and its color changed to black. The solution was subsequently stirred into approximately 2 l of ice-water and acidified to pH=3 using 10% strength HCl, and the precipitate was filtered off with suction.

Yield: 13.6 g (65%). $^1$H-NMR(270 MHz, $CDCl_3$): 2.4 (s, 3H); 3.9 (s, 3H); 6.8 (d, 1H); 6.95 (d, 1H); 7.42 (d, 1H); 10.6 (s, 1H).

b) 3-Bromo-2-methoxy-6-methylsulfanylbenzaldehyde

Bromine (28.8 g, 0.18 mol) (dissolved in dioxane (500 ml)) was added dropwise to a solution of 2-methoxy-6-methylsulfanylbenzaldehyde (22 g, 0.12 mol) in dioxane (500 ml), and the mixture was stirred at 50° C. for 6 h. The mixture was then concentrated, the residue was taken up in $CH_2Cl_2$, and the mixture was washed with $H_2O$, dried over $MgSO_4$ and concentrated. The solid was recrystallized from diisopropyl ether.

Yield: 17.5 g (56%). $^1$H-NMR(270 MHz, $CDCl_3$): 2.40 (s, 3H); 3.90 (s, 3H); 6.72 (d, 1H); 6.85 (d, 1H); 7.42 (m, 1H); 10.6 (s, 1H).

c) 1-Bromo-2-methoxy-4-methylsulfanyl-3-vinylbenzene

At 0° C., potassium tert-butoxide (6.2 g, 55.4 mmol) was added to a solution of methyltriphenylphosphonium bromide (19.7 g, 55.4 mmol) in THF (180 ml). At from −10 to −5° C., 3-bromo-2-methoxy-6-methylsulfanylbenzaldehyde (12 g, 46 mmol) dissolved in THF (180 ml) was then added, and the mixture was stirred overnight at RT for 7 h. The mixture was filtered, and the solution was admixed with $H_2O$ (200 ml) and MTBE (200 ml) and then extracted with MTBE (200 ml). The combined organic phases were dried over $MgSO_4$ and concentrated. Chromatography (cyclohexanez→cyclohexane/EtOAc 9:1) gave 1-bromo-2-methoxy-4-methylsulfanyl-3-vinylbenzene.

Yield: 4.67 g (39%). $^1$H-NMR(270 MHz, $CDCl_3$): 2.40 (s, 3H); 3.70 (s, 3H); 5.62 (dd, 1H); 5.90 (dd, 1H); 6.70–6.90 (m, 2H); 7.40 (s, 1H).

d) 2-Methoxy-4-methylsulfanyl-3-vinylbenzoic acid

At −100° C., n-BuLi (25 ml, 15% strength in n-hexane, 4.1 mmol) was added to a solution of 1-bromo-2-methoxy-4-methylsulfanyl-3-vinylbenzene (7 g, 31.3 mmol) in THF (300 ml), and the mixture was stirred at −100° C. for 20 min. At −100° C., $CO_2$ was then introduced (exothermic reaction up to −60° C.). At -80 to −90° C., the mixture was then stirred for another 1 h, and NaOH (100 ml) was added dropwise at −40° C. The solution was stirred into EtOAc (400 ml), and the mixture was extracted 3× with 5% strength NaOH and acidified to a pH=1 using 10% strength HCl. The $H_2O$ phase was extracted with EtOAc (300 ml), and the combined organic phases were dried over $MgSO_4$ and concentrated.

Yield: 6.8 g (98%). $^1$H-NMR(270 MHz, $CDCl_3$): 1.90 (s, 3H); 2.42 (s, 3H); 3.62 (s, 3H); 5.50–5.80 (m, 2H); 6.58–6.65 (m, 1H); 7.1 (d, 1H); 7.6 (d, 1H).

e) 4-Methylsulfonyl-2-methoxy-3-vinylbenzoic acid $NaWO_4$ (cat.) was added to a solution of 2-methoxy-4-methylsulfanyl-3-vinylbenzoic acid (6.8 g, 30 mmol) in AcOH (130 ml), $H_2O_2$ (8.6 ml, 76 mmol) was added dropwise, and the mixture was stirred at room temperature for 5 h. The solution was concentrated, the residue was taken up in methylene chloride, and the mixture was dried over magnesium sulfate and concentrated.

Yield: 4.8 g (61%). $^1$H-NMR(270 MHz, $CDCl_3$): 3.20 (s, 3H); 3.70 (s, 3H); 5.65–5.90 (m, 2H); 7.0–7.20 (m, 1H); 7.65–7.95 (m, 2H).

f) 5-Hydroxy-1-cyclopropyl-1H-pyrazol-4-yl-(4-methylsulfonyl-2-methoxy-3-vinylphenyl)methanone $SOCl_2$ (1.2 g, 10 mmol) was added to a solution of 4-methylsulfonyl-2-methoxy-3-vinylbenzoic acid (1.6 g, 6 mmol) in toluene (60 ml), and the mixture was heated at reflux for 2 h. The mixture was then concentrated, and the product was added to a solution of N-cyclopropylpyrazolone (6 mmol), $K_2CO_3$ (1.6 g, 11.6 mmol) in DME (30 ml), and the mixture was stirred at RT overnight. The mixture was subsequently heated at reflux for 2 h and concentrated, and the residue was dissolved in $H_2O$. The $H_2O$ phase was extracted 3× with $CH_2Cl_2$, and the combined organic phases were dried over $MgSO_4$ and concentrated.

EXAMPLE 2

In the manner as described in Example 1, it is possible to obtain the following compounds:

TABLE 2.1

Ia1

| Ex. No. | $R^1$ | $R^7$ | M.p. [° C.] |
|---|---|---|---|
| 2.01 | O—CH$_3$ | cyclopropyl | 155–157 |
| 2.02 | Cl | cyclopropyl | 200–204 |
| 2.03 | CH$_3$ | cyclopropyl | 155–158 |
| 2.04 | O—CH$_3$ | Cyclopentyl | 139–140 |
| 2.05 | Cl | Cyclopentyl | |
| 2.06 | CH$_3$ | Cyclopentyl | |
| 2.07 | O—CH$_3$ | norbornyl | |
| 2.08 | Cl | norbornyl | |
| 2.09 | CH$_3$ | norbornyl | |
| 2.10 | O—CH$_3$ | 2,7,7-trimethylnorbornyl | |
| 2.11 | Cl | 2,7,7-trimethylnorbornyl | |
| 2.12 | CH$_3$ | 2,7,7-trimethylnorbornyl | |
| 2.13 | O—CH$_3$ | 2-adamantyl | |
| 2.14 | Cl | 2-adamantyl | |
| 2.15 | CH$_3$ | 2-adamantyl | |
| 2.16 | O—CH$_3$ | 7-adamantyl | |
| 2.17 | Cl | 7-adamantyl | |
| 2.18 | CH$_3$ | 7-adamantyl | |
| 2.19 | OC$_2$H$_5$ | cyclopropyl | 150–153 |
| 2.20[1] | OCH$_3$ | cyclopropyl | oil |

[1]Compound I where $R^{16}$ = 4-methylphenylsulfonyloxy

EXAMPLE 3

The compounds below can be prepared in the same manner as described in Example 1:

TABLE 3.1

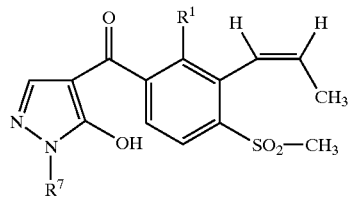

Ia3

| Ex. No. | $R^1$ | $R^7$ | M.p. [° C.] |
|---|---|---|---|
| 3.01 | CH$_3$ | cyclopropyl | 91–106 |
| 3.02 | O—CH$_3$ | cyclopropyl | |
| 3.03 | Cl | cyclopropyl | |
| 3.04 | CH$_3$ | cyclopentyl | |
| 3.05 | O—CH$_3$ | cyclopentyl | |
| 3.06 | Cl | cyclopentyl | |

EXAMPLE 4

The herbicidal activity of the compounds of the formula I was demonstrated by greenhouse experiments:

The culture containers used were plastic pots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of 3 to 15 cm, depending on the plant habit, and then treated with the active compounds which had been suspended or emulsified in water. The test plants were for this purpose either sown directly and grown in the same containers, or they were first grown separately as seedlings and transplanted into the test containers a few days prior to treatment.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments are preferably composed of the following species:

| Code | Common name |
|---|---|
| AMARE | pigweed |
| CHEAL | lambsquarters |
| ECHCG | barnyardgrass |
| POLPE | ladysthumb |
| SETVI | green foxtail |

| Code | Common name |
| --- | --- |
| SINAL | white mustard |
| SOLNI | black nightshade |

At 0.25 kg of a.s. (active substance)/ha, the compounds I according to the invention, applied pre-emergence, effect very good control of harmful grasses and/or broad-leaved plants. The compounds according to the invention thus have pronounced herbicidal action.

TABLE 4.1

Herbicidal activity on post-emergence application in the greenhouse (application rate: 0.25 kg of active substance/ha)

| Compound from Ex. No. | Test plants | Assessment scale |
| --- | --- | --- |
| 2.02 | AMARE | 95 |
| 2.02 | CHEAL | 100 |
| 2.02 | ECHCG | 85 |
| 2.02 | SEFTA | 80 |
| 2.03 | AMARE | 95 |
| 2.03 | CHEAL | 98 |
| 2.03 | ECHCG | 95 |
| 2.03 | SEFTA | 95 |
| 3.01 | AMARE | 98 |
| 3.01 | CHEAL | 98 |
| 3.01 | ECHCG | 95 |
| 3.01 | SEFTA | 95 |

We claim:
1. A pyrazole of the formula I

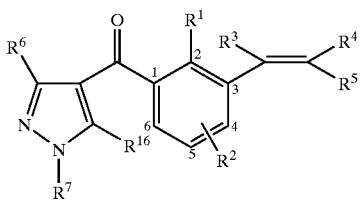

where:
R$^1$ is hydrogen, nitro, halogen, cyano, thiocyanato, $C_1$–$C_6$-alkyl, $C_1$–$C_6$-alkoxy, $C_1$–$C_6$-haloalkyl, $C_1$–$C_6$-alkylthio, $C_1$–$C_6$-alkoxy-$C_1$–$C_6$-alkyl, $C_2$–$C_6$-alkenyl, $C_2$–$C_6$-alkynyl, —S(O)$_n$R$^8$, —SO$_2$OR$^9$, —SO$_2$NR$^9$R$^{10}$, —NR$^{10}$SO$_2$R$^{11}$, —NR$^{10}$COR$^{11}$, —PO(OR$^{12}$)(OR$^{13}$);

R$^2$ is hydrogen, $C_1$–$C_6$-alkyl, $C_1$–$C_6$-alkoxy, $C_1$–$C_6$-alkylthio, $C_2$–$C_6$-alkenyl, $C_2$–$C_6$-alkynyl, halogen, nitro, —S(O)$_n$R$^8$, —SO$_2$OR$^9$, —SO$_2$NR$^9$R$^{10}$, —NR$^{10}$SO$_2$R$^{11}$, —NR$^{10}$COR$^{11}$, —PO(OR$^{12}$)(OR$^{13}$);

R$^3$ is hydrogen, halogen, $C_1$–$C_6$-alkyl, $C_1$–$C_6$-haloalkyl, $C_1$–$C_6$-alkoxy, $C_2$–$C_6$-alkenyl or $C_2$–$C_6$-alkynyl;

R$^4$, R$^5$ are hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —COR$^{12}$, —CO$_2$R$^{12}$, —COSR$^{12}$, —CONR$^{12}$R$^{13}$, —C(R$^{14}$)=NR$^{15}$, —PO(OR$^{12}$)(OR$^{13}$), $C_1$–$C_4$-alkyl carrying a radical from the following group: —COR$^{12}$, —CO$_2$R$^{12}$, —COSR$^{12}$, —CONR$^{12}$R$^{13}$ or —C(R$^{14}$)=NR$^{15}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, where the six last-mentioned radicals may be substituted by one to three halogen atoms and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl; or $C_1$–$C_4$-alkoxycarbonyl; and where heterocyclyl alone and in composed form is a three- to seven-membered saturated or partially unsaturated mono- or polycyclic heterocycle which contains one to three heteroatoms selected from a group consisting of oxygen, nitrogen and sulfur; and where heteroaryl alone and in composed form is an aromatic or polycyclic radical which, in addition to carbon ring members, may additionally contain one to four nitrogen atoms or one to three nitrogen atoms and one oxygen or one sulfur atom or one oxygen or one sulfur atom; or R$^4$ and R$^5$ together form a $C_2$–$C_6$-alkanediyl chain which can be mono- to tetrasubstituted by $C_1$–$C_4$-alkyl and/or may be interrupted by oxygen or sulfur or an unsubstituted or $C_1$–$C_4$-alkyl substituted nitrogen;

R$^6$ is hydrogen, halogen, $C_1$–$C_6$-alkyl, $C_1$–$C_6$-alkoxy, $C_3$–$C_8$-cycloalkyl;

R$^7$ is $C_3$–$C_{14}$-cycloalkyl, $C_3$–$C_{14}$-cycloalkenyl or a carbocyclic bi- or tricyclic system selected from the group consisting of adamantyl, camphyl, camphenyl and norbornyl;

n is 0, 1 or 2;

R$^8$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

R$^9$ is hydrogen, $C_1$–$C_6$-alkyl, $C_1$–$C_6$-aloalkyl, $C_1$–$C_6$-alkoxy-$C_2$–$C_6$-alkyl, $C_3$–$C_6$-alkenyl or $C_3$–$C_6$-alkynyl;

R$^{10}$ is hydrogen or $C_1$–$C_6$-alkyl;

R$^{11}$ is $C_1$–$C_6$-alkyl or $C_1$–$C_6$-haloalkyl;

R$^{12}$ is hydrogen, $C_1$–$C_6$-alkyl, $C_3$–$C_6$-cycloalkyl, $C_1$–$C_6$-haloalkyl, $C_3$–$C_6$-alkenyl, $C_3$–$C_6$-alkynyl, phenyl or benzyl, where the two last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

R$^{13}$ is hydrogen, $C_1$–$C_6$-alkyl, $C_3$–$C_6$-alkenyl or $C_3$–$C_6$-alkynyl; or R$^{12}$ and R$^{13}$ together form a $C_2$–$C_6$-alkanediyl chain which may be mono- to tetrasubstituted by $C_1$–$C_4$-alkyl and/or may be interrupted by oxygen or sulfur or an unsubstituted or $C_1$–$C_4$-alkyl-substituted nitrogen;

R$^{14}$ is hydrogen, $C_1$–$C_6$-alkyl, $C_1$–$C_6$-haloalkyl, $C_1$–$C_6$-alkoxy, $C_1$–$C_6$-alkoxycarbonyl, $C_3$–$C_6$-cycloalkyl, $C_2$–$C_6$-alkenyl, $C_2$–$C_6$-alkynyl, phenyl or benzyl, where the two last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

R$^{15}$ is $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkoxy, $C_1$–$C_6$-haloalkoxy, $C_3$–$C_6$-cycloalkoxy, $C_3$–$C_6$-alkenyloxy, $C_3$–$C_6$-alkynyloxy, phenyl, benzyl or benzyloxy, where the three last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

$R^{16}$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, phenyl-$C_1$–$C_4$-alkoxy, phenylcarbonyloxy, phenylcarbonyl-$C_1$–$C_4$-alkoxy, phenylsulfonyloxy, where the phenyl radical of the four last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

and their tautomers and agriculturally useful salts.

2. A pyrazole as claimed in claim 1, where $R^7$ is as defined below: cyclopropyl, cyclobutyl, cyclopentyl or cyclohexyl.

3. A pyrazole as claimed in claim 1, where $R^2$ is in the 4 position of the phenyl ring and is as defined below: —$SO_2R^8$, —$SO_2OR^9$ and $R^9$ and $R^8$ are each $C_1$–$C_6$-alkyl.

4. A pyrazole as claimed in claim 1, where $R^3$ is hydrogen or $C_1$–$C_6$-alkyl.

5. A pyrazole as claimed in claim 1, where $R^4$ is hydrogen or $C_1$–$C_6$-alkyl.

6. A pyrazole as claimed in claim 1, where $R^5$ is hydrogen, $C_1$–$C_6$-alkyl, $C_1$–$C_6$-alkoxy or cyano.

7. A pyrazole as claimed in claim 1, where $R^3$, $R^4$ and $R^5$ are in each case identical and are hydrogen.

8. A pyrazole as claimed in claim 1, where $R^1$ is halogen, $C_1$–$C_6$-alkoxy or $C_1$–$C_6$-alkyl.

9. A pyrazole as claimed in claim 1, where $R^{16}$ is hydroxyl.

10. A process for preparing pyrazoles as claimed in claim 1, which comprises acylating a pyrazole of the formula II

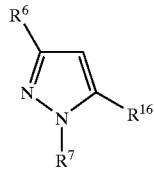

with a carboxylic acid III or an activated derivative thereof

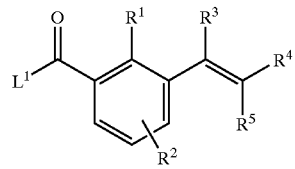

where the variables $R^1$ to $R^7$ are as defined under claim 1 and $L^1$ is hydroxyl or a nucleophilically displaceable leaving group, and rearranging the acylation product, if appropriate in the presence of a catalyst, to give the compounds I.

11. A composition, comprising a herbicidally effective amount of at least one pyrazole of the formula I or an agriculturally useful salt of I as claimed in claim 1 and auxiliaries which are customary for formulating crop protection agents.

12. A process for preparing herbicidally effective compositions as claimed in claim 10, which comprises mixing a herbicidally effective amount of at least one pyrazole of the formula I or an agriculturally useful salt of I and auxiliaries which are customary for formulating crop protection agents.

13. A method for controlling undesirable vegetation, which comprises allowing a herbicidally effective amount of at least one pyrazole of the formula I or an agriculturally useful salt of the latter as claimed in claim 1 to act on plants, their habitat and/or on seed.

* * * * *